(12) United States Patent
Berglund

(10) Patent No.: US 6,630,431 B2
(45) Date of Patent: Oct. 7, 2003

(54) NAIL POLISH LACQUER REMOVER

(75) Inventor: Kris A. Berglund, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 10/146,973

(22) Filed: May 16, 2002

(65) Prior Publication Data

US 2002/0183215 A1 Dec. 5, 2002

Related U.S. Application Data

(60) Provisional application No. 60/295,279, filed on Jun. 1, 2001.

(51) Int. Cl.[7] .................................................. C11D 3/44
(52) U.S. Cl. ........................ 510/118; 510/417; 510/424; 510/477; 510/488; 510/505; 252/364; 424/61; 424/401; 424/702.1
(58) Field of Search ................................. 510/477, 424, 510/417, 118, 488, 505, 421; 252/364; 424/61, 401, 702.1

(56) References Cited

U.S. PATENT DOCUMENTS

| | | | |
|---|---|---|---|
| 4,735,798 A | | 4/1988 | Bernstein |
| 5,360,580 A | * | 11/1994 | Dotolo et al. ............... 510/118 |
| 5,372,742 A | | 12/1994 | Bayless |
| 5,486,305 A | | 1/1996 | Farynlarz et al. |
| 6,046,148 A | * | 4/2000 | Toussaint et al. ........... 510/235 |
| 6,096,699 A | * | 8/2000 | Bergemann et al. ........ 510/201 |
| 6,284,720 B1 | * | 9/2001 | Opre .......................... 510/170 |
| 6,395,103 B1 | * | 5/2002 | Machac et al. ............... 134/40 |

FOREIGN PATENT DOCUMENTS

JP     57122013     7/1982

* cited by examiner

*Primary Examiner*—Gregory E. Webb
(74) *Attorney, Agent, or Firm*—Ian C. McLeod

(57) ABSTRACT

A composition which is a mixture of a hydroxylated carboxylic acid ester and a mono-, di- or tricarboxylic acid ester for solvating a nail polish lacquer for removal is described. Included are kits for compositions for and a method of using the compositions.

6 Claims, No Drawings

NAIL POLISH LACQUER REMOVER

CROSS-REFERENCE TO RELATED APPLICATIONS

This application claims the benefit of Provisional Application No. 60/295,279, filed Jun. 1, 2001.

None

STATEMENT REGARDING FEDERALLY SPONSORED RESEARCH AND DEVELOPMENT

None

BACKGROUND OF THE INVENTION

1. Field of the Invention

The present invention relates to a nail polish lacquer remover which is non-toxic, non-flammable and environmentally benign. In particular, the present invention relates to a composition, kit and method which comprises a liquid mixture of a hydroxylated carboxylic acid ester and a dicarboxylic acid diester which is a solvent for the lacquer.

2. Description of Related Art

Nail polish, sometimes referred to as nail polish lacquer, must be removed from nails without damage to the nail or to health of the individual. At present, most commercial finger nail polish removers utilize acetone, which is flammable and highly volatile, as the base for a liquid formulation. A second class of removers utilize ethyl acetate as the base which is also flammable and highly volatile.

The following patents are representative of the prior art. JP 54046846 (1979) teaches the use of gamma butyrolactone, methyl acetate, water, and perfumes as the basis for the formulation. This formulation is claimed to be noncombustible. A number of other compounds are described which are different from those of the present invention. JP 57122013 (1982) claims an acetone, water, and 2-octyldodecyl oleate mixture. U.S. Pat. No. 4,735,798 (1988) claims an acetone, ethyl acetate, ethanol, water, and glycerin mixture with a claim of improved adhesion of the nail polish subsequent to use of the remover.

Two (2) U.S. patents separately describe the use of succinate or lactate esters.

In Bayless (U.S. Pat. No. 5,372,742), the solvent d-limonene which is a skin irritant is used in the formulations. In addition, ethyl acetate and cetyl acetate are claimed as essential. The present invention does not use either limonene or cetyl acetate. In Farynlarz et al (U.S. Pat. No. 5,486,305), a volatile component, acetone, is described as essential, in addition to a $C_4$ to $C_{30}$ diester, and water. These formulations do not include hydroxylated carboxylic acid esters (e.g. ethyl lactate) and requires that one component be a volatile solvent. Thus solvents such as acetone and limonene are required in these formulations. These components are flammable and toxic.

SUMMARY OF THE INVENTION

The present invention relates to a composition for removing nail polish lacquer which comprises as a mixture:

(a) a hydroxylated carboxylic acid ester which is liquid at STP; and (b) a dicarboxylic acid diester which is a liquid at STP, wherein the mixture is a solvent for the nail polish lacquer.

Further, the present invention relates to a composition for removing nail polish which comprises as a mixture:

(a) ethyl lactate; and (b) diethyl succinate, wherein the mixture is a solvent for nail polish.

The present invention also relates to a nail polish lacquer removing composition comprising as a mixture:

(a) for the lacquer 1 to 10 part by volume of ethyl lactate;

(b) 1 to 10 part by volume of diethylsuccinate; and (c) optionally up to about 0.1 part by volume water based upon (a) and (b).

The present invention also relates to a nail polish lacquer removing composition which comprises in admixture:

(a) a liquid hydroxylated mono, di- or tri-carboxylic acid ester, wherein the hydroxylated mono- , di- or trihydroxylated acid moiety is selected from the group consisting of lactic, malic, citric and tartaric acids and mixtures thereof, and the ester moiety is lower alkyl containing 1 to 4 carbon atoms; and (b) a liquid dicarboxylic acid diester of the formula

wherein $R_1$ and $R_2$ are lower alkyl containing 1 to 4 carbon atoms, which can be the same or different, and x is an integer of 1 to 4.

The present invention also relates to a method for removing a dried nail lacquer from the nail which comprises:

(a) applying a composition comprising as a mixture a hydroxylated carboxylic acid ester which is liquid at STP; and a dicarboxylic acid diester which is a liquid at STP, wherein the mixture is a solvent for the nail polish lacquer so as to solvate the nail polish on the nail; and (b) removing the solvated nail polish from the nail.

The present invention also relates to a method for removing a dried nail polish lacquer from the nail which comprises:

(a) applying a composition which comprises a mixture ethyl lactate; and diethyl succinate, wherein the mixture is a solvent for nail polish to solvate the nail polish on the nail; and (b) removing the solvated nail polish from the nail.

The present invention relates to a method for removing a dried nail polish lacquer from the nail which comprises:

(a) applying a composition comprising as a mixture 1 to 10 part by volume of ethyl lactate; 1 to 10 part by volume of diethylsuccinate; and optionally up to about 0.1 part by volume water based upon (a) and (b) to solvate the nail polish lacquer on the nail; and (b) removing the solvated nail polish from the nail.

The present invention also relates to a method for removing a nail polish lacquer from the nail which comprises:

(a) applying a composition as a mixture which comprises a liquid hydroxylated mono, di- or tri-carboxylic acid ester wherein the acid moiety is selected from the group consisting of lactic, malic, citric and tartaric acids and mixtures thereof, and the ester moiety is alkyl containing 1 to 4 carbon atoms; and a liquid dicarboxylic acid diester of the formula

wherein $R_1$ and $R_2$ are lower alkyl containing 1 to 4 carbon atoms which can be the same or different and x is 1 to 4 to solvate the nail polish lacquer on the nail;

(b) removing the solvated nail polish from the nail.

The present invention also relates to a kit for solvating nail polish lacquer which comprises:

(a) a composition which comprises as a mixture a hydroxylated carboxylic acid ester which is liquid at STP and a dicarboxylic and diester which is liquid at STP, wherein the mixture is a solvent for the nail polish lacquer in a sealable container; and (b) an applicator in the container which is removable from the container for applying the composition to the nail to solvate the nail polish lacquer for removal.

The present invention also relates to a kit for solvating nail polish lacquer which comprises:

(a) a composition which comprises as a mixture ethyl lactate; and diethylsuccinate, wherein the mixture is a solvent for nail polish lacquer; and (b) an applicator in the container and removable from the container for applying the composition to the nail.

The present invention also relates to a kit for solvating nail polish lacquer which comprises:

(a) a composition which comprises as a mixture lacquer 1 to 10 part by volume of ethyl lactate; 1 to 10 part by volume of diethyl succinate; and optionally up to about 0.1 part by volume water based upon the lactate and succinate in a sealable container; and (a) an applicator in the container which seals the container and which is removable from the container for applying the composition to the nail to solvate the nail polish lacquer for removal.

The present invention also relates to a kit for solvating nail polish lacquer which comprises:

(a) a composition as a mixture which comprises a liquid hydroxylated mono, di- or tri-carboxylic acid ester wherein the acid moiety is selected from the group consisting of lactic, malic, citric and tartaric acids and mixtures thereof, and the ester moiety is alkyl containing 1 to 4 carbon atoms; and a liquid dicarboxylic acid diester of the formula

wherein $R_1$ and $R_2$ are lower alkyl containing 1 to 4 carbon atoms which can be the same or different and x is 1 to 4 in a sealable container; and (b) an applicator which is removable from the container for applying the composition to the solvate the nail polish lacquer from removal.

In particular, lactate-succinate ester blends are excellent nail polish lacquer removing solvents which are non-toxic. The preferred embodiment of the invention uses ethyl lactate and diethyl sucinate in equal volume proportions. These esters are miscible with each other in all proportions. In addition, some water can be added to the mixture, however, above about 10% by volume water a two phase solution will be formed which is no longer a good polish remover.

DESCRIPTION OF PREFERRED EMBODIMENTS

The present invention uses a combination of esters homologous to lactate and succinate esters. We have particularly found that combinations of ethyl lactate with diethyl succinate are excellent nail polish removers, but are not toxic and have very low volatility and flammability. In addition, these formulations are biodegradable and possess a very small environmental impact.

Ethyl lactate and diethyl succinate are both listed as acceptable ingredients for synthetic flavorings and adjuvants in 21CFR172.515, 21CFR172 is "Food Additives Permitted For Direct Addition to Food For Human Consumption." The LD50 data shows that very large doses are required to produce toxic results in animals. These solvents are thus the most preferred.

A ternary diagram for the system diethyl succinate, ethyl-1-lactate and water at 297° K. The reference is Uusi-Pentilla, M., R. J. Richards, P. Blowers, B. A. Torgerson, and K. A. Berglund, "Liquid-Liquid Equilibria of Selected Dibasic Ester+Water+Solvent Ternary Systems," *J. Chem. Eng. Data* 1996, 41, 235–238. This diagram shows that the limit of solubility of water in the mixture is about 10%.

The dielectric constant for ethyl lactate is 16.5 and for diethyl succinate is 6.7 as reported by Uusi-Pentilla, M., R. J. Richards, B. A. Torgerson, and K. A. Berglund, "Spectroscopically Determined Dielectric Constants for Various Esters," Ind. Eng. Chem. Res. 1997, 36, 510–512. The succinate is non-polar and the lactate is polar and thus, it is surprising that the compositions of the present invention are so effective.

The vapor pressure of ethyl lactate is 1.6 mmHg @ 20° C. and for diethyl succinate is 0.2 mmHg @ 20° C. These are very favorable for a nail polish removing lacquer.

Other hydroxylated carboxylic acid esters can be used in place of the lactates including, but not limited to, malic, citric, and tartaric. Other aliphatic carboxylic acid esters preferably containing 1 to 8 carbon atoms can be used in place of the succinates including, but not limited to, glutaric and adipic. The alcohol used to make the esters can include, but are not limited to, methanol, ethanol, n-propanol, isopropanol, isobutanol, and n-butanol which are lower alkanols containing 1 to 4 carbon atoms. Other non-solvent ingredients such as surfactants, detergents, and fragrances can be used as additives in the formulation. They can be used as adjuvants, extenders and olfactory agents.

EXAMPLE 1

A 50:50 volume percent solution of ethyl lactate and diethyl succinate was made. The resulting solution was water clear and was easily adsorbed onto a paper tissue that was subsequently used to remove finger nail polish lacquer from the finger nails of a thirteen-year-old female. The polish was completely removed with ease and no damage to the nail was observed and no damage or drying of the skin was observed.

EXAMPLE 2

A 50:50 volume percent solution of ethyl lactate and diethyl succinate was made. The resulting solution was water clear and was easily adsorbed onto a tissue that was subsequently used to remove finger nail polish lacquer from a glued-on imitation nail extender. The polish was completely removed with ease and no damage to the imitation or natural nail was observed.

A repeat patch test with the 50:50 by volume mixture of diethylsuccinate and ethyl lactate showed that there was no response. Thus the compositions of the present invention are safe for use as a nail polish.

The compounds used in the present invention can be produced from natural sources of succinic acid and lactic acid. The acids are produced by fermentation.

It is intended that the foregoing description be only illustrative of the present invention and that the present invention be limited only by the hereinafter appended claims.

I claim:

1. A method for removing a dried nail polish lacquer from a nail which consists essentially of:
   (a) applying a composition which comprises a hydroxylated carboxylic acid ester wherein the hydroxylated carboxylic acid moiety is selected from the group consisting of lactic acid, malic acid, citric acid and tartaric acid and mixtures thereof and the ester moiety is lower alkyl containing 1 to 4 carbon atoms and a lower alkyl succinic acid diester, wherein lower alkyl contains 1 to 4 carbon atoms, to the dried nail polish lacquer on the nail to solvate the dried nail polish lacquer on the nail; and
   (b) removing the composition and solvated nail polish lacquer from the nail.

2. The method of claim 1 wherein the ratio by volume of the hydroxylated carboxylic acid ester to the succinic acid diester is between about 1 to 10 and 10 to 1.

3. A method for removing a dried nail polish lacquer from a nail which consists essentially of:
   (a) applying a composition which comprises ethyl lactate and diethyl succinate to the dried nail polish lacquer on the nail to solvate the dried nail polish lacquer on the nail; and
   (b) removing the composition and solvated nail polish lacquer from the nail.

4. The method of claim 3 wherein the ratio by volume of the ethyl lactate to the diethyl succinate is between about 1 to 10 and 10 to 1.

5. The method of claim 1 wherein the hydroxylated carboxylic acid moiety of the hydroxylated carboxylic acid ester is derived from malic acid, citric acid and tartaric acid and mixtures thereof, and the ester moiety is alkyl containing 1 to 4 carbon atoms.

6. A method for removing a dried nail polish lacquer from a nail which consists essentially of:
   (a) applying a composition which comprises 1 to 10 part by volume of ethyl lactate; 1 to 10 part by volume of diethylsuccinate; and optionally up to about 0.1 part by volume water based upon lactate and succinate to the dried nail polish lacquer on the nail to solvate the dried nail polish lacquer on the nail; and
   b) removing the composition and solvated nail polish lacquer from the nail.

* * * * *